United States Patent [19]

Remih

[11] 4,167,938

[45] Sep. 18, 1979

[54] EXERCISER FOR VAGINAL MUSCLES

[76] Inventor: Harry Remih, Hierzigsberg 2, Remich, Luxembourg

[21] Appl. No.: 761,451

[22] Filed: Jan. 21, 1977

[30] Foreign Application Priority Data

Sep. 28, 1976 [DE] Fed. Rep. of Germany ....... 2643514

[51] Int. Cl.$^2$ .............................................. A61B 5/10
[52] U.S. Cl. .................................. 128/778; 128/25 R; 128/79; 128/344
[58] Field of Search ............. 128/2 S, 344, 343, 24 R, 128/25 R, 79; 73/744

[56] References Cited

U.S. PATENT DOCUMENTS

| | | | |
|---|---|---|---|
| 612,724 | 10/1898 | Hamilton | 128/344 |
| 1,523,290 | 1/1925 | Rimailho | 73/744 S |
| 2,541,520 | 2/1951 | Kegel | 128/2 S |
| 2,839,050 | 6/1958 | Sokol | 128/2 S |
| 3,752,150 | 8/1973 | Harris | 128/2 S |

FOREIGN PATENT DOCUMENTS 240189  8/1969  U.S.S.R. .................................. 128/2 S

*Primary Examiner*—Robert W. Michell
*Assistant Examiner*—Michael H. Thaler
*Attorney, Agent, or Firm*—Robert W. Beach; Ward Brown

[57] ABSTRACT

A distensible body having an air impervious bladder of stretchable material is connected to a compressed air source and to a pressure indicator by hoses. A squeeze bulb and a releasable check valve pumping air into the body force the stretchable bladder to distend. The bladder pressure is shown on the pressure indicator which can be entirely mechanical or can include electronic components providing a digital display of such pressure.

When relaxed, the body is inserted into the vagina and then the body bladder is distended until it engages the vaginal wall. The elasticity of the vaginal muscles is measured by noting the increase in bladder pressure indicated as more air is pumped into the body. Controlled exercise of the vaginal muscles is effected by alternately distending the body bladder to exert a predetermined amount of pressure on the vaginal wall and releasing the pressure by allowing air to escape through the releasable check valve.

6 Claims, 5 Drawing Figures

EXERCISER FOR VAGINAL MUSCLES

BACKGROUND OF THE INVENTION

1. Field of the Invention

The present invention relates to apparatus for the controlled exercise and measurement of the elasticity of the vaginal muscles.

2. Prior Art

It is known that the firmness of vaginal muscles varies among different women, that such muscles can become flaccid with increasing age, and that flaccid muscles can be made firmer by exercise. No exerciser is known which allows the controlled exercise and measurement of the elasticity of the vaginal muscles.

SUMMARY OF THE INVENTION

The principal object of the present invention is to provide an exerciser for the controlled exercise and measurement of the elasticity of the vaginal muscles.

This object can be accomplished by providing a distensible body which can be inserted into the vagina when such body is in a relaxed state and which then can be distended to apply a predetermined amount of pressure on the vaginal wall. The distensible body can have an air impervious bladder of stretchable material which bladder can be forced to distend by pumping air from a compressed air source into the body. A pressure indicator can be provided to show the bladder pressure and can be entirely mechanical or can include electronic components providing a digital display.

In one embodiment, the bladder of the distensible body is tubular and has its opposite ends clamped to the opposite ends of a spool of catenoidal shape. Such clamping is accomplished at one end of the spool by the snaphead of a core member having a shank extending substantially through the spool bore and at the other end of the spool by a joining member screwed into the core member shank. Passages are provided so that air from the compressed air source can travel through the joining and core members and through the spool to the inside of the bladder.

DETAILED DESCRIPTION

Figure 1:
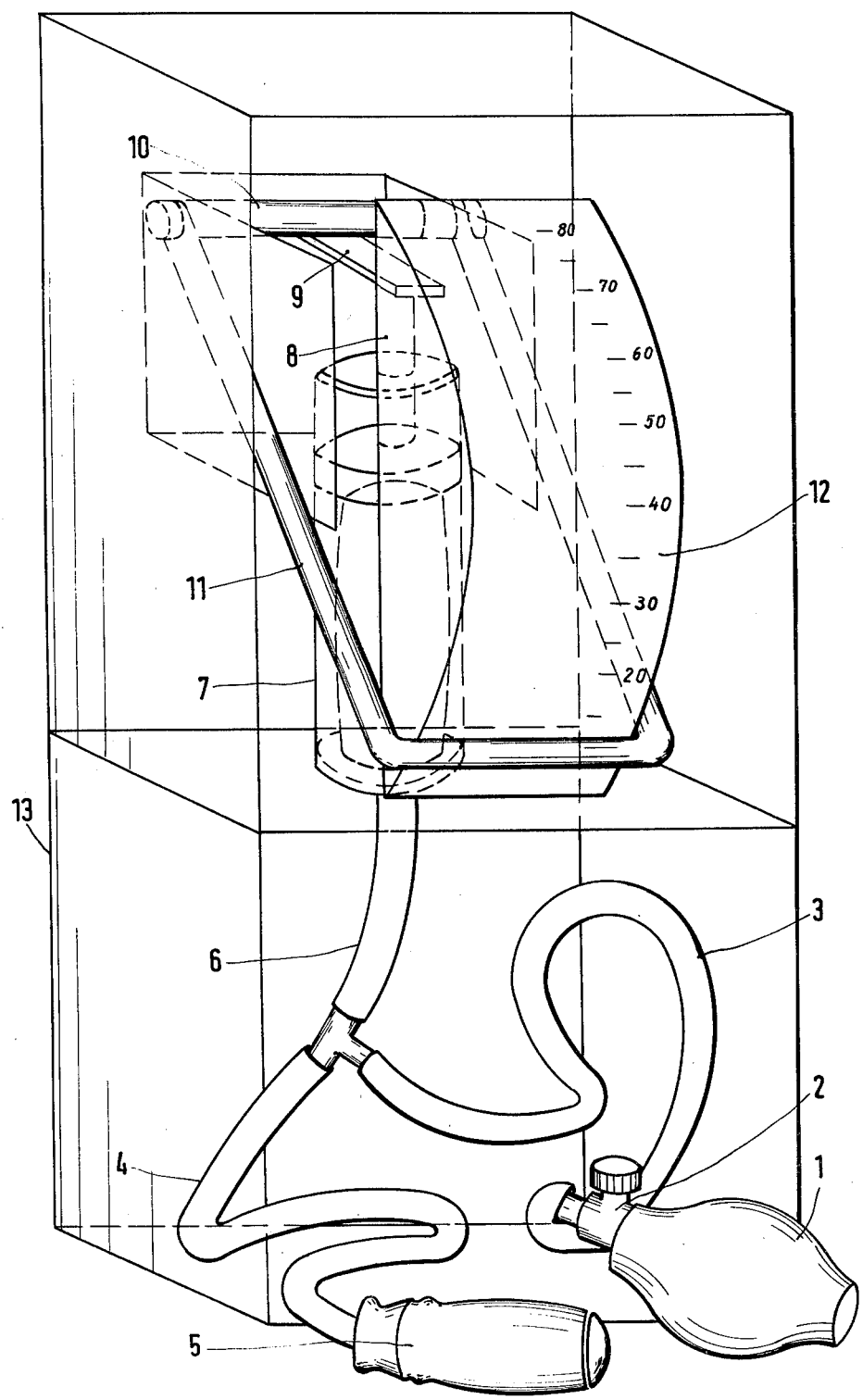
FIG. 1 is a perspective of an exerciser in accordance with the present invention including a distensible body, a compressed air source and a pressure indicator.

The exerciser shown in FIG. 1 has a compressed air source including a conventional squeeze bulb 1 and a releasable check valve 2 that permits air to pass into a hose 3 when the bulb is squeezed but prevents air from returning through the hose when the bulb is released. Hose 3 communicates with two other hoses 4 and 6 through a tee connection. Hose 4 extends from the tee to a body 5 which is insertable into the vagina and which can be circumferentially expanded by distension. Hose 6 extends from the tee to a pressure indicator.

Figure 2:
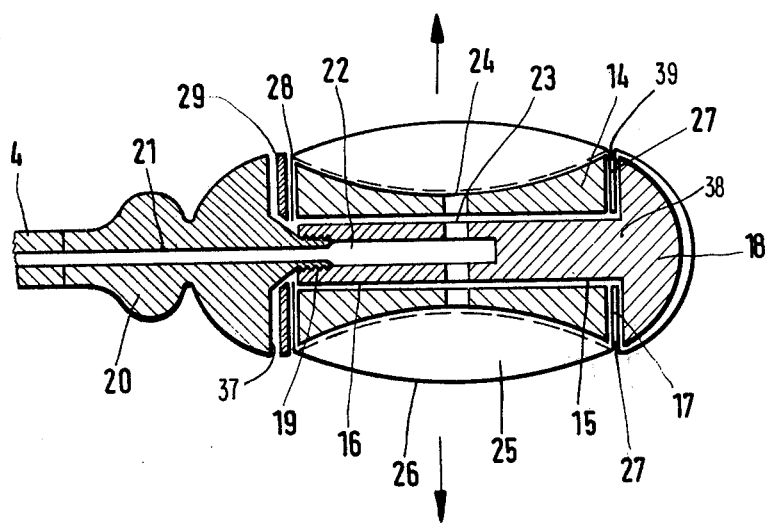
FIG. 2 is a longitudinal central section of the distensible body shown in FIG. 1.

As best seen in FIG. 2, hose 4 communicates with the inside of the distensible body through the axial bore 21 of an elongated joining member 20. The end of the joining member remote from hose 4 forms an annular flange 37. An externally threaded stem 19 extends outward from the central portion of such flange and is screwed into a blind axial bore 22 in the shank portion 16 of a core member 38. To permit easy insertion of the body into the vagina, the core member has a snaphead 18. The inside of such snaphead forms another annular flange 39 spaced from and facing flange 37.

A spool or rigid member 14, having a circumference of generally catenoidal shape, is loosely carried on the shank 16 of the core member and is encircled by a thin tubular bladder 26. The bladder is made of an air impervious stretchable material, and the opposite bladder ends 27 and 28 are clamped to the opposite ends of the spool. To prevent the bladder from twisting as stem 19 of joining member 20 is screwed into the shank of the core member, end 28 is clamped between one end of the spool and a retaining washer 29 carried by the stem. The opposite bladder end 27 is clamped between the opposite end of the spool and the snaphead 18 of core member 38.

A pair of diametral ducts 23 and 24 in the core shank 16 and spool 14, respectively, provide a passage from the blind axial bore 22 in the shank to the inside of the bladder. In FIG. 2, the ducts are shown as being substantially aligned, but even if they were not aligned air could travel through duct 23, around shank 16 and then through a duct 24 because the diameter of the spool bore is larger than the diameter of the shank. With this arrangement, air can travel freely between hose 4 and the inside of the bladder.

Figure 3:
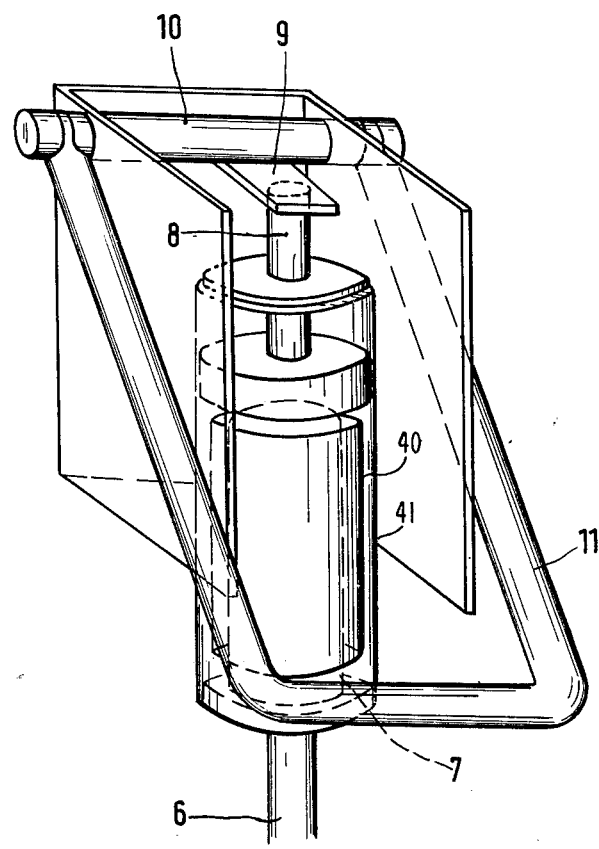
FIG. 3 is a perspective of the pressure indicator shown in FIG. 1.

In the mechanical pressure indicator shown in FIGS. 1 and 3, hose 6 communicates with an elongated, longitudinally extendible air cell 7. The air cell is confined against transverse distension by an open-ended cylinder 40 within an outer cylinder 41. The outer cylinder receives a piston and rod 8 with the piston resting on the upward end of air cell 7 and the rod extending longitudinally of the cylinder away from the air cell. An increase in pressure in hose 6 communicated to the air cell will extend it longitudinally and force the piston and rod upward.

The free end of rod 8 is positioned directly under a tongue 9 which extends transversely from a pivot 10. Such pivot is mounted with its axis of rotation in a plane substantially perpendicular to the axis of the piston rod and the pivot's outward end portions carry the ends of a U-shaped pointer 11. Lengthwise movement of the piston rod will rotate pivot 10, thereby swinging the pointer. As shown in FIG. 1, a scale 12 can be provided so that the pressure in hose 6 can be gauged by the position of pointer 11 relative to the scale.

Figure 4:
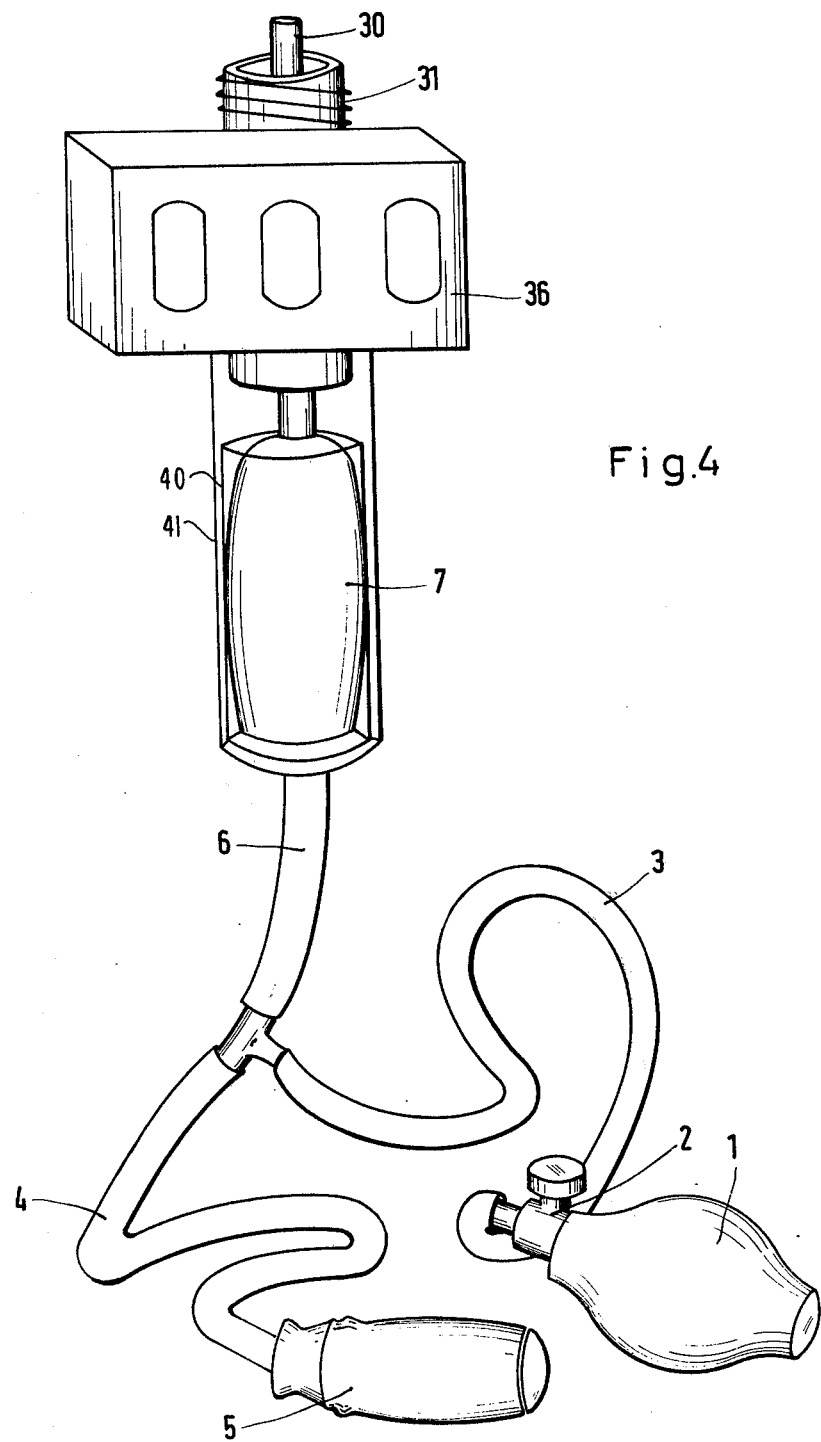
FIG. 4 is a perspective of another exerciser in accordance with the present invention including a digital display pressure indicator.
Figure 5:
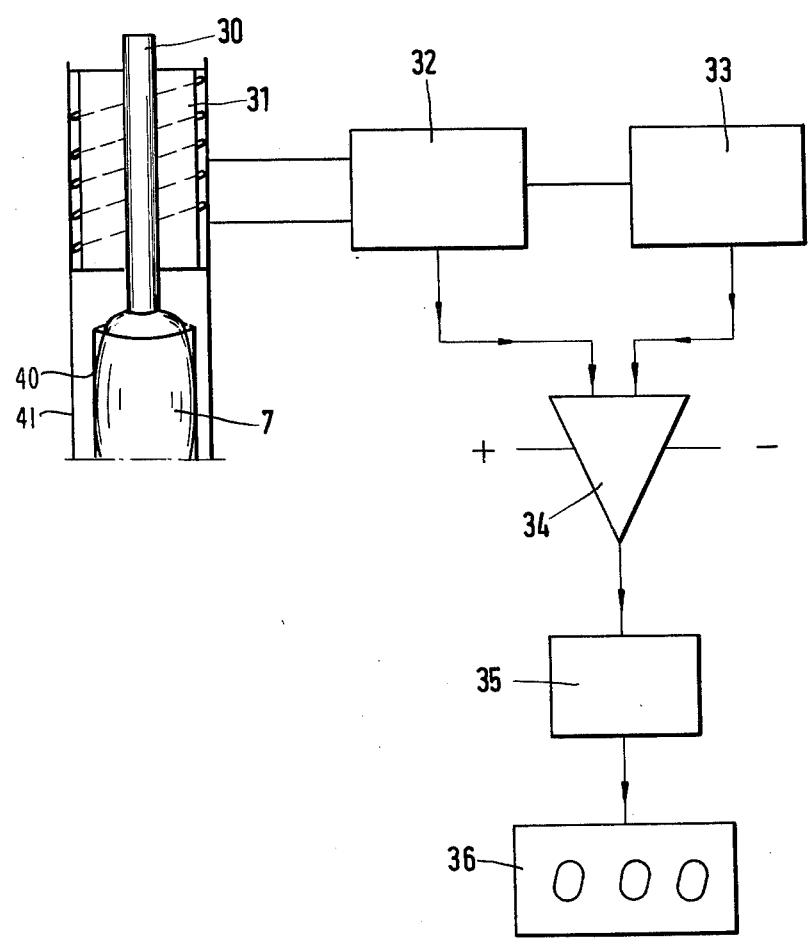
FIG. 5 is a block circuit diagram of the pressure indicator shown in FIG. 4.

The modified pressure indicator shown in FIGS. 4 and 5 provides a digital display. As in the mechanical pressure indicator, hose 6 communicates with a transversely confined, elongated air cell 7. However, extension of the air cell in this indicator causes an armature 30 to extend through an electromagnetic coil 31. Such coil is connected to a detunable oscillator 32 whose output varies according to the amount of extension of the armature through the coil. The output of the detunable oscillator and the output of a constant oscillator 33 are fed into a comparator 34 which is powered by a battery (indicated by the plus and minus signs in FIG. 5). The comparator switches a counter 35 and a digital display 36 according to the sum of the outputs of the two oscillators.

In operation, a suitable pressure indicator of an exerciser in accordance with the present invention is placed in position for viewing and a relaxed body 5 is inserted into the vagina. Air is pumped into the body by squeezing the squeeze bulb 1, thereby forcing the bladder 26 to distend, for example from the broken line position of FIG. 2 to the solid line position in that figure. The bladder will engage the vaginal wall and the underlying vaginal muscles will resist further distension of the bladder. Introduction of more air into the body will result in an increase in bladder pressure which will be shown on the pressure indicator. The elasticity of the vaginal muscles can be measured by noting the pressure shown as more air is introduced into the distensible body.

A controlled exercise of the vaginal muscles can be achieved by pumping air into an inserted distensible body, as described above, until a desired amount of pressure is exerted on the vaginal wall and underlying vaginal muscles. The pressure exerted should be sufficient to stretch the vaginal muscles at least slightly. Air can then be released through the adjustable check valve and the vaginal muscles will contract to their relaxed condition. The process can be repeated whereby the vaginal muscles will alternately be stretched and contract.

I claim:

1. In an exerciser for vaginal muscles including expandable means insertable into a vagina for engaging the vaginal wall and operating means for effecting expansion of the expandable means and thereby exerting pressure on such wall, such expandable means including an elongated rigid member having an axial bore and a radial duct intersecting such bore, a tubular bladder of air impervious stretchable material generally encircling the rigid member and means for clamping longitudinally spaced portions of the bladder between longitudinally spaced portions of the rigid member and the clamping means, the rigid member radial duct being located between such longitudinally spaced portions of the rigid member, the improvement comprising the clamping means including a core member having a shank portion received in the axial bore of the rigid member and a head portion forming a flange for clamping one end portion of the bladder to one end of the rigid member, the clamping means further including a joining member connected to said shank portion of said core member and having a flange for clamping the other end portion of the bladder to the other end of the rigid member.

2. In the exerciser defined in claim 1, the expandable means being distensible by the introduction of a fluid under pressure therein, the operating means including means for supplying fluid under pressure to the expandable means, and indicating means for indicating the amount of pressure exerted on the vaginal wall by distension of the expandable means.

3. In the exerciser defined in claim 2, the indicating means including cell means for extending in response to an increase in pressure within said cell means, hose means connecting the expandable means and said cell means, rod means movable axially by extension of said cell means, pivot means mounted substantially perpendicular to said rod means and rotatable by axial movement of said rod means, pointer means carried by said pivot means for swinging about the axis of said pivot means upon rotary movement of said pivot means, and scale means for gauging the amount of swing of said pointer means.

4. In the exerciser defined in claim 2, the indicating means including cell means for extending in response to an increase in pressure within said cell means, hose means connecting the expandable means and said cell means, electric coil means and armature means movable through said coil means by extension of said cell means, first oscillator means for supplying a varying output depending on the degree of extension of said armature means through said coil means, second oscillator means for supplying a constant output, comparator means for receiving said oscillator outputs, and counter means and display means both of which are switched by said comparator means for indicating the pressure within said cell means.

5. In the exerciser defined in claim 1, the joining member being threadedly connected to the core member shank portion such that relative turning of the joining member and the core member in a given direction draws the core member head portion toward the joining member to clamp the respective opposite end portions of the bladder to the respective opposite ends of the rigid member.

6. In the exerciser defined in claim 1, the joining member having a passage therethrough for receiving fluid under pressure from the operating means, and the core member shank portion having an axial bore and a diametral duct intersecting said shank portion bore for receiving such fluid from said joining member passage and for conveying such fluid to the axial bore of the rigid member.

* * * * *

UNITED STATES PATENT AND TRADEMARK OFFICE
CERTIFICATE OF CORRECTION

PATENT NO. : 4,167,938

DATED : September 18, 1979

INVENTOR(S) : Harry Remih

It is certified that error appears in the above–identified patent and that said Letters Patent are hereby corrected as shown below:

Title page, under [30] Foreign Application Priority Data, insert --Oct. 9, 1976 [DE] Fed. Rep. of Germany ...2645758--.

*Signed and Sealed this*

*Twenty-ninth* Day of *July 1980*

[SEAL]

*Attest:*

SIDNEY A. DIAMOND

*Attesting Officer*  *Commissioner of Patents and Trademarks*